(12) United States Patent
Jimenez et al.

(10) Patent No.: US 12,702,566 B2
(45) Date of Patent: Aug. 11, 2026

(54) EXPANDABLE INTEVERTEBRAL CAGE

(71) Applicant: Octagon Spine LLC, Seattle, WA (US)

(72) Inventors: Omar Fernando Jimenez, Seattle, WA (US); Yefim I. Safris, Golden Valley, MN (US)

(73) Assignee: Octagon Spine, Inc., Seattle, WA (US)

(*) Notice: Subject to any disclaimer, the term of this patent is extended or adjusted under 35 U.S.C. 154(b) by 457 days.

(21) Appl. No.: 18/208,472

(22) Filed: Jun. 12, 2023

(65) Prior Publication Data

US 2024/0407928 A1 Dec. 12, 2024

(51) Int. Cl.

| | |
|---|---|
| ***A61F 2/44*** | (2006.01) |
| ***A61F 2/46*** | (2006.01) |
| *A61F 2/30* | (2006.01) |

(52) U.S. Cl.

CPC .......... *A61F 2/4455* (2013.01); *A61F 2/4611* (2013.01); *A61F 2002/30092* (2013.01); *A61F 2002/30146* (2013.01); *A61F 2002/30579* (2013.01); *A61F 2002/4653* (2013.01); *A61F 2310/00023* (2013.01); *A61F 2310/00071* (2013.01)

(58) Field of Classification Search

CPC .............. A61F 2/44–447; A61F 2/4611; A61F 2002/30092; A61F 2002/30146; A61F 2002/30579; A61F 2002/4653; A61F 2310/00023; A61F 2310/00071

See application file for complete search history.

(56) References Cited

U.S. PATENT DOCUMENTS

| | | | | |
|---|---|---|---|---|
| 7,951,199 | B2 | 5/2011 | Miller | |
| 8,523,944 | B2 | 9/2013 | Jimenez | |
| 8,540,452 | B2 | 9/2013 | Jimenez | |
| 9,445,918 | B1 | 9/2016 | Lin | |
| 11,234,835 | B2 | 2/2022 | Jimenez | |
| 11,497,622 | B2 | 11/2022 | Jimenez | |
| 12,011,365 | B2 | 6/2024 | Jimenez | |
| 2002/0177897 | A1 | 11/2002 | Michelson | |
| 2006/0184231 | A1* | 8/2006 | Rucker | A61F 2/90 623/1.15 |
| 2007/0225726 | A1 | 9/2007 | Dye | |

(Continued)

OTHER PUBLICATIONS

International Search Report & Written Opinion, dated Apr. 29, 2020, Application No. PCT/US2019/068890.

(Continued)

*Primary Examiner* — Nicholas J Plionis
(74) *Attorney, Agent, or Firm* — Merchant & Gould P.C.

(57) ABSTRACT

Disclosed herein are systems and methods for intervertebral body fusion that provide more robust support within the disc space. Intervertebral body fusion devices can have a unitary monolithic body including a plurality of body segments interconnected with each other by flexure members. Devices can be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted. Changes between the expansion and compression configurations can be controlled based on the temperature of the device.

9 Claims, 12 Drawing Sheets

(56) References Cited

U.S. PATENT DOCUMENTS

| | | | | |
|---|---|---|---|---|
| 2008/0243255 | A1* | 10/2008 | Butler | A61F 2/4465 623/17.11 |
| 2012/0083887 | A1 | 4/2012 | Purcell | |
| 2012/0209386 | A1* | 8/2012 | Triplett | A61F 2/4465 623/17.16 |
| 2014/0058512 | A1 | 2/2014 | Petersheim | |
| 2014/0277490 | A1 | 9/2014 | Perloff | |
| 2015/0230929 | A1 | 8/2015 | Lorio | |
| 2015/0245900 | A1* | 9/2015 | Eaton | A61F 2/848 623/1.12 |
| 2015/0272745 | A1 | 10/2015 | Jimenez et al. | |
| 2017/0056179 | A1* | 3/2017 | Lorio | B23K 15/0093 |
| 2017/0056200 | A1 | 3/2017 | Koch et al. | |
| 2018/0021149 | A1 | 1/2018 | Boehm | |
| 2020/0281739 | A1* | 9/2020 | Jimenez | A61F 2/4611 |
| 2020/0281743 | A1* | 9/2020 | Jimenez | A61F 2/447 |

OTHER PUBLICATIONS

International Search Report & Written Opinion, dated Aug. 21, 2023, Application No. PCT/US2023/028048.

* cited by examiner

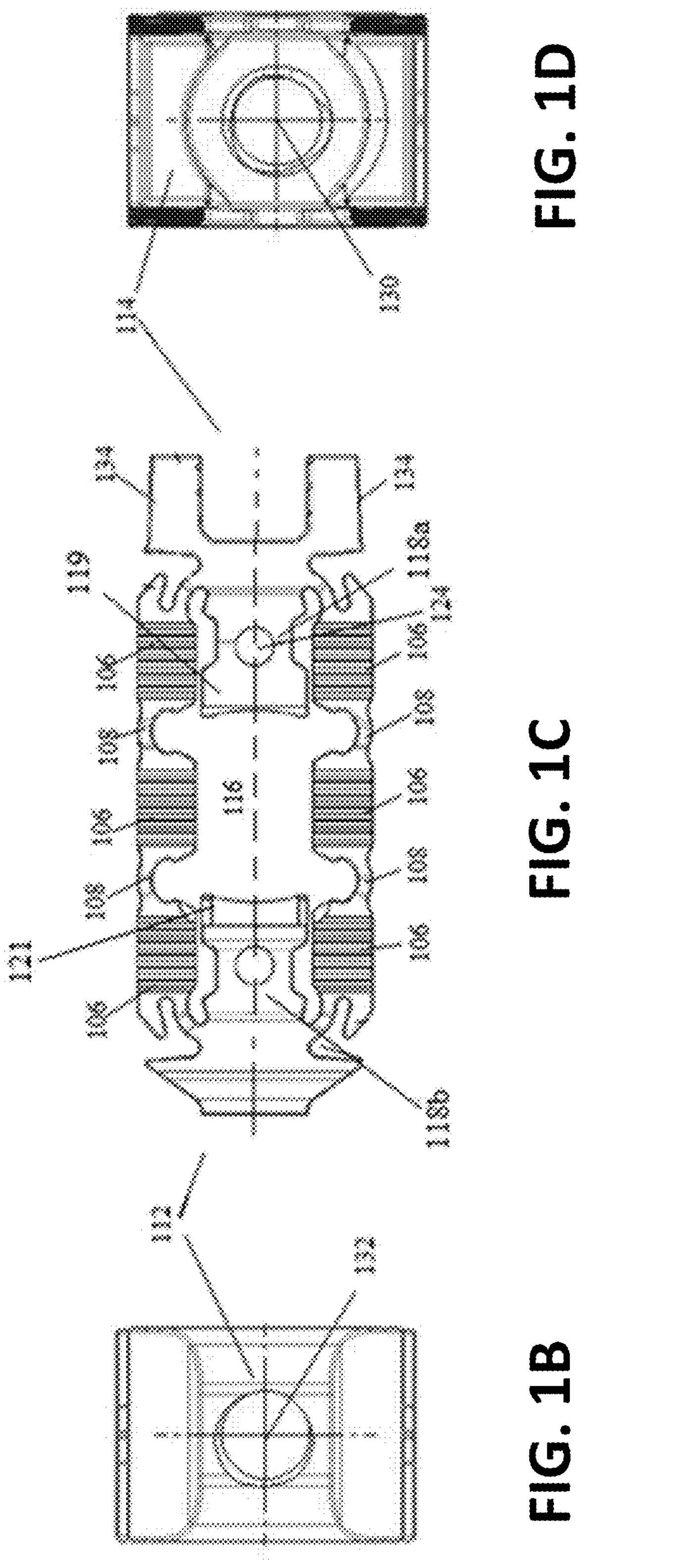
FIG. 1D
FIG. 1C
FIG. 1B
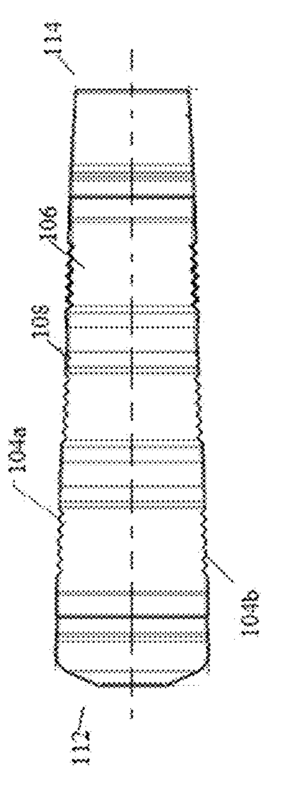
FIG. 1E

EXPANDABLE INTEVERTEBRAL CAGE

TECHNICAL FIELD

The present disclosure relates to the fusion of vertebral bodies. More specifically, the present disclosure relates to devices and associated methods for fusion of vertebral bodies that provide robust spinal support in a less invasive manner.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone-to-bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce a distraction device that will distract a collapsed disc in a generally axial direction, decompress the nerve root, and allow load sharing to enhance bone formation, and then implant an intervertebral fusion device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space such that the vertebral bodies are separated in a generally axial direction by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral distraction and fusion can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

As with all minimally invasive surgeries, a primary goal is to provide equivalent or near equivalent treatment as more invasive surgical techniques but with less discomfort, recovery time, etc. for the patient. One problem with minimally invasive intervertebral fusion procedures is that the limited size of the surgical access limits the size of the implant(s) that can be inserted. While devices that are vertically expandable in a generally axial direction have addressed some of these issues by being able to be inserted through a smaller opening and then made taller in a generally axial direction within the disc space, such devices are still limited in the transverse footprint that can be covered within the disc space which can affect the stability of the device within the disc space and limits the area for bone grown. Examples of such devices are disclosed in U.S. Pat. No. 11,234,835 and U.S. Patent Publication No. 2020/0281743, each of which is incorporated herein by reference in its entirety.

SUMMARY

Non-limiting examples of the present disclosure provide an expandable intervertebral body fusion device, comprising a unitary monolithic body comprising a shape memory material. The unitary monolithic body having a plurality of body segments coupled to each other with flexure members and an opening defined between the plurality of body segments, wherein the body is configured to automatically mediolaterally expand from a compressed configuration to an expanded configuration when the body exceeds a threshold temperature, causing the plurality of body segments to generally move away from each other and expand the opening between the plurality of body segments such that the body forms a greater mediolateral footprint in the expanded configuration than in the compressed configuration. The body is configured to automatically mediolaterally retract from the expanded configuration a compressed configuration when the body falls below the threshold temperature, causing the plurality of body segments to retract back into the compressed configuration and reduce the mediolateral footprint.

In embodiments, the body of the expandable intervertebral body fusion device, once expanded, maintains the expanded configuration when the temperature of the body exceeds the threshold temperature.

In embodiments, the body expands into the expanded configuration and is maintained based on the internal body temperature of a patient, in which the body is implanted.

In embodiments, expansion of the body occurs at a temperature between 33° C. and 37° C.

In embodiments, the unitary monolithic body is constructed of Nitinol material.

In embodiments, the plurality of body segments includes adjacent projections and grooves that form tongue and groove connections between adjacent mediolateral body segments when the body is in the expanded configuration, the tongue and groove connections providing increased resistance of the body to shear and torsional forces.

One example of the present disclosure provides an expandable intervertebral body fusion device, comprising a unitary monolithic body having a plurality of body segments coupled to each other with flexure members and an opening defined between the plurality of body segments. A first locking bushing extending from a first end body into the opening and a second locking bushing extending from a second end body segment into the opening. The body is configured to be mediolaterally expanded from a compressed configuration to an expanded configuration causing one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration, and wherein the first and second locking bushings are brought together within the opening and further expansion of the body is prevented by the interaction between the first and second locking bushing.

In embodiments, the intervertebral body fusion device is constructed by wire EDM.

In embodiments, the first locking bushing or the second locking busing are attached to the body with an expansion tool, wherein a plurality of locking bushings having different axial lengths, wherein each different axial length is configured to permit a predetermined amount of expansion of the body.

One example of the present disclosure provides a method for operating an expandable intervertebral body fusion device comprising providing a unitary monolithic fusion device in a collapsed configuration, wherein the collapsed configuration is maintained when the device is below a threshold temperature and implanting the device into a body of a patient, in the collapsed configuration, wherein the device expands into an expanded configuration at the threshold temperature from an increase in temperature from the body of the patient in which the device is implanted.

In embodiments, the method further comprises constructing the intervertebral body fusion device by wire EDM.

In embodiments, the method further comprises cooling the device with a cooling solution that expedites transitioning from the expanded configuration to the collapsed configuration.

In embodiments, the method further comprising removing the device from the body following cooling of the device.

In embodiments, the method further comprises expanding the body at a temperature between 33° C. and 37° C.

In embodiments, the method further comprises expanding the body into the expanded configuration and maintaining the expanded configured, based on an internal body temperature of a user.

In embodiments, the method further comprises constructing the unitary monolithic body out of Nitinol material.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1F depict an expandable intervertebral body fusion device in a collapsed configuration according to an embodiment.

Figure 1A:
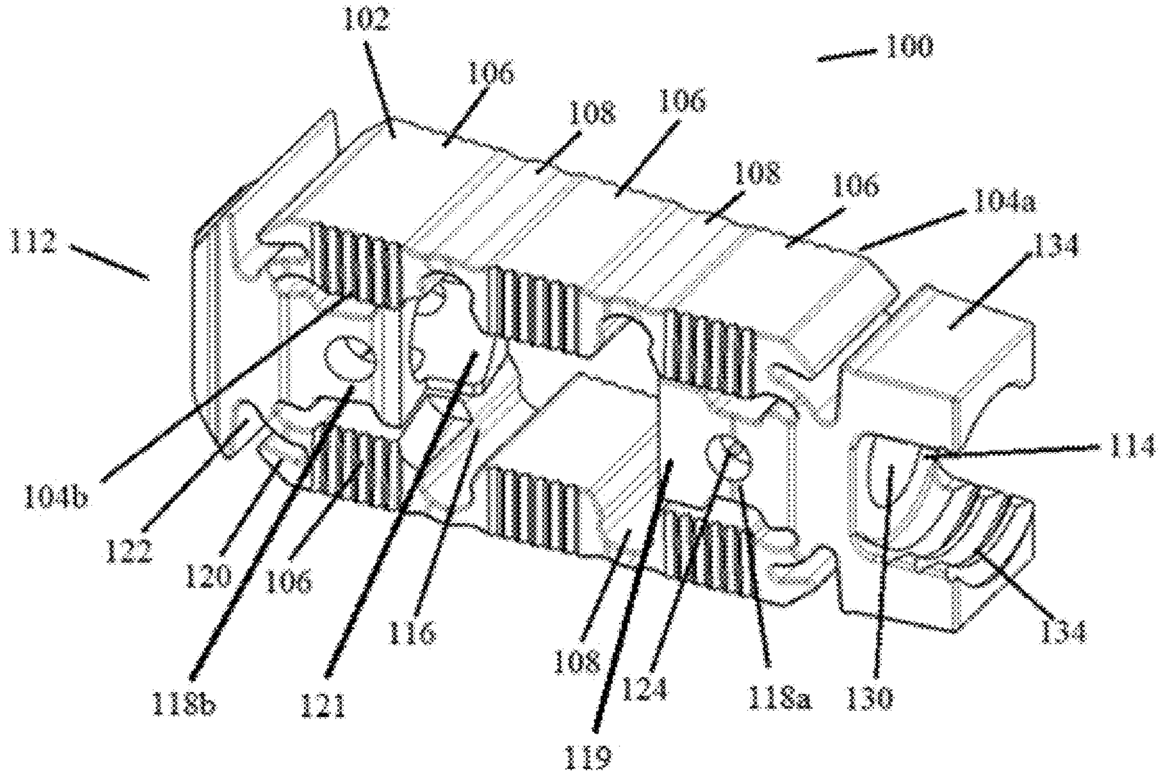
Figure 1F:
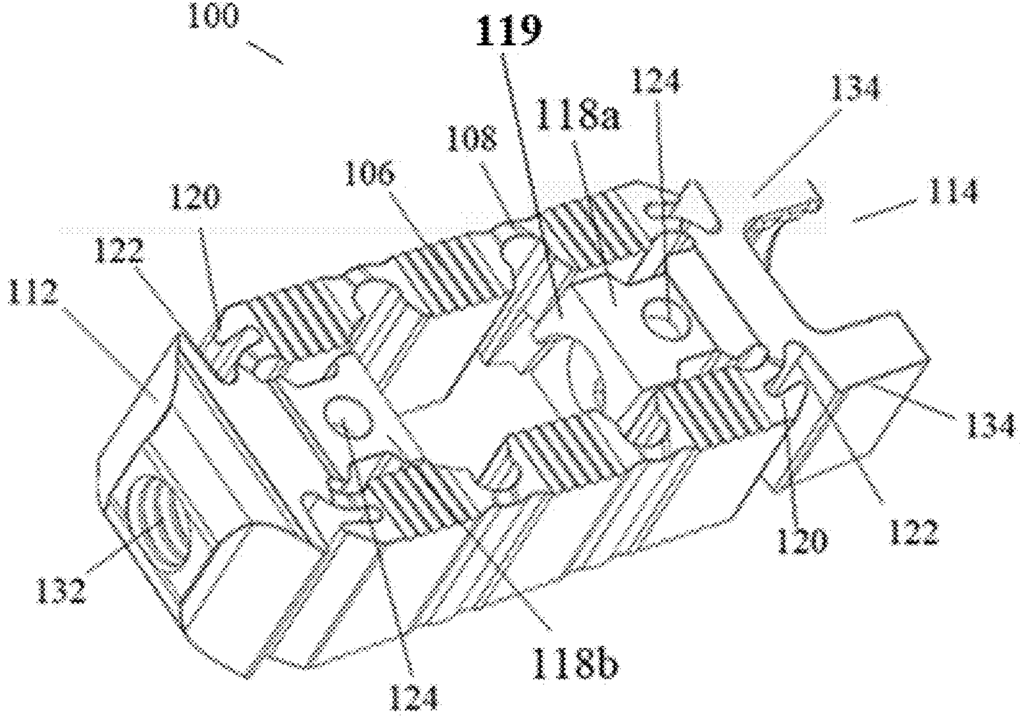
Figure 2A:
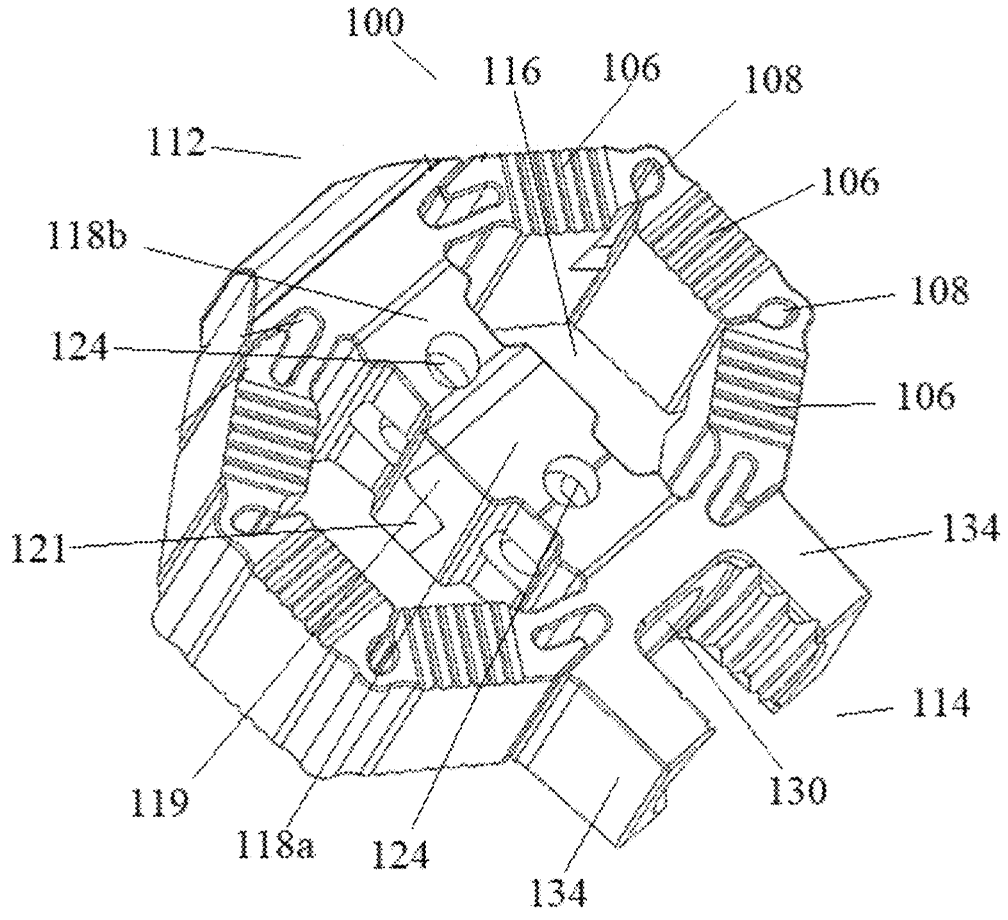
FIGS. 2A-2F depict the expandable intervertebral body fusion device of FIGS. 1A-1F in an expanded configuration.
Figure 2B:
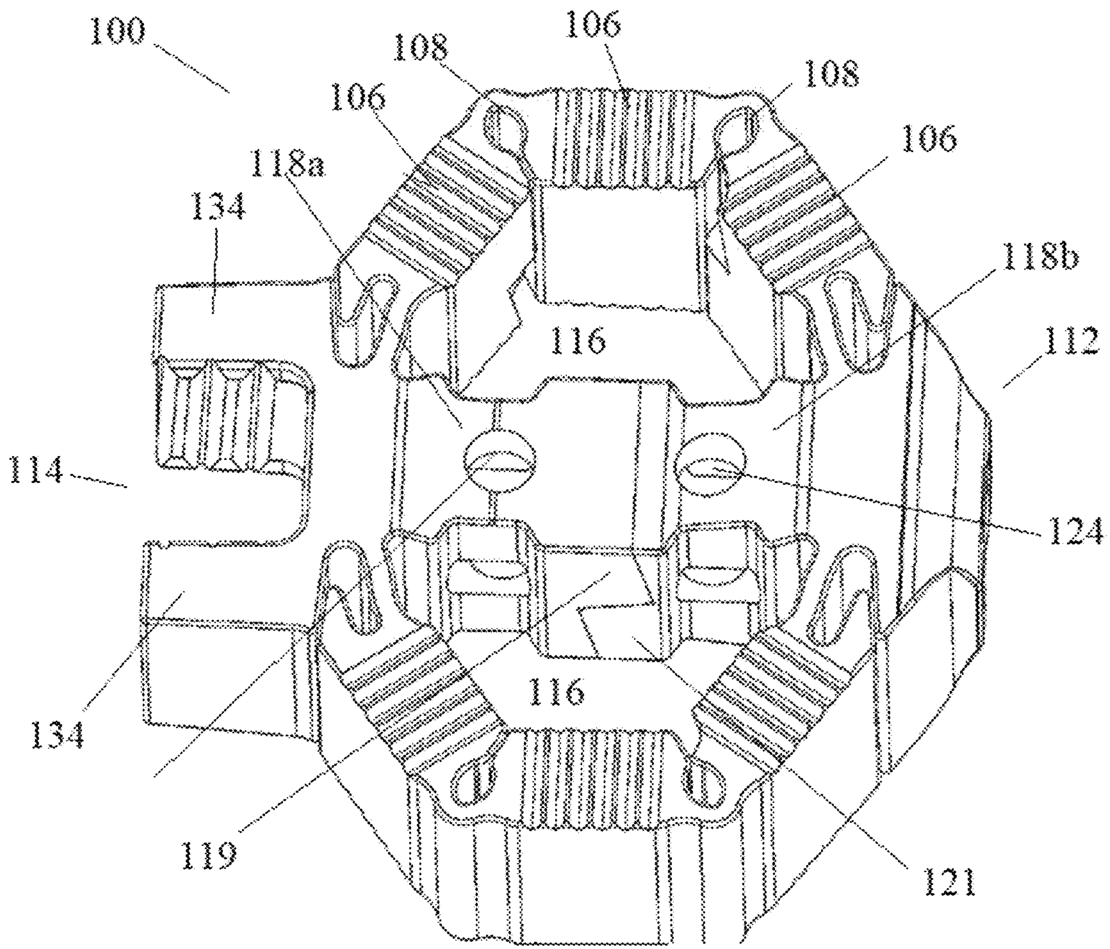
Figure 2C:
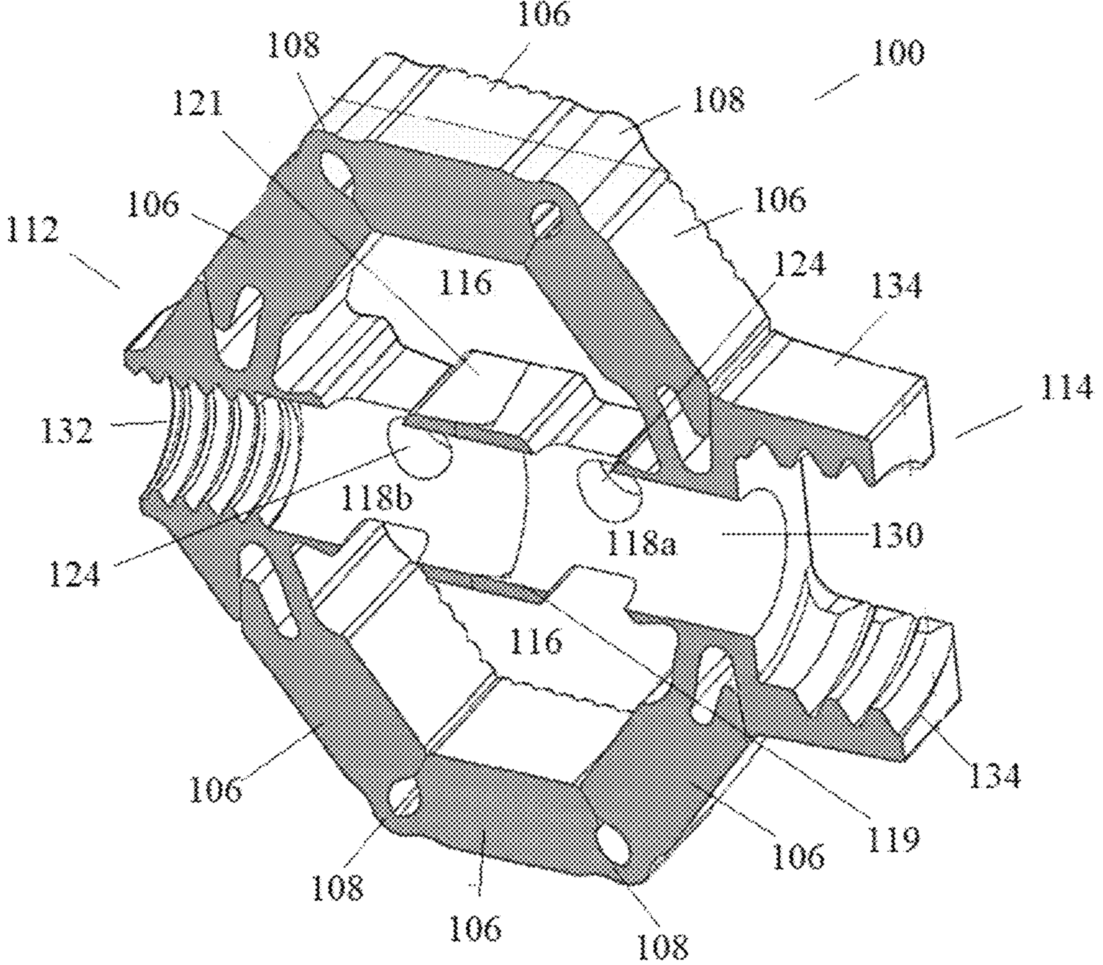
Figures 2D, 2E, 2F:
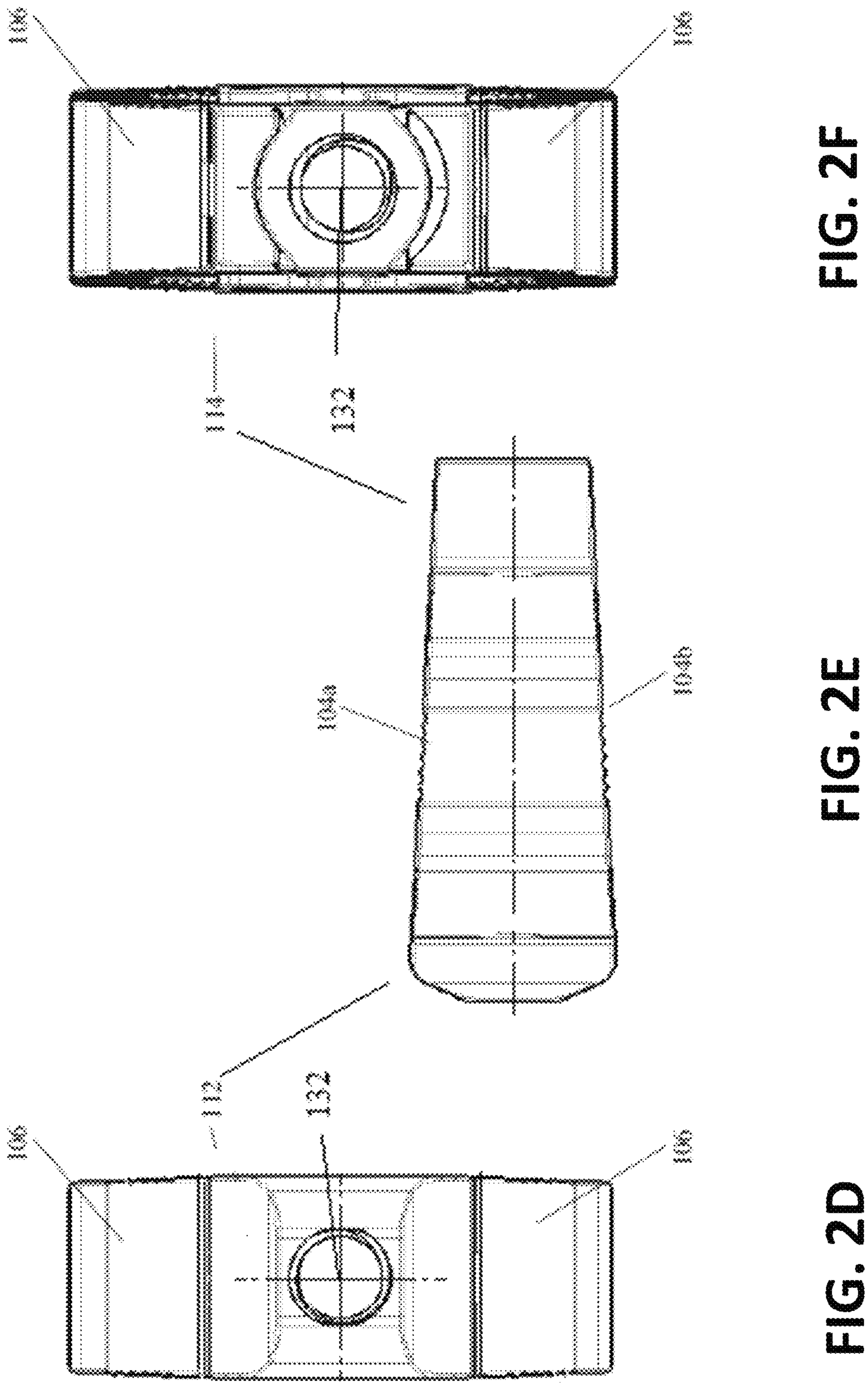

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Reference now will be made in detail to embodiments of the disclosure, one or more examples of which are illustrated in the drawings. Each example is provided by way of explanation in the disclosure and is not limited thereto. In fact, it will be apparent to those skilled in the art that various modifications and variations can be made in the present disclosure without departing from the scope of the disclosure. For instance, features illustrated or described as part of one embodiment can be used with another embodiment to yield a still further embodiment.

FIGS. 1A-1F and 2A-2E depict an expandable intervertebral body fusion device 100 according to an embodiment. FIGS. 1A-1F depict device 100 in a collapsed configuration and FIGS. 2A-2E depict device 100 in an expanded configuration. In practice, device 100 can be inserted into the disc space through a minimally invasive access in the collapsed configuration and then expanded inside of the disc space. In embodiments, device 100 can be inserted between adjacent vertebrae on its side (i.e., as shown in FIG. 1E) such that when it is expanded in the disc space it expands horizontally/transversely to the disc space to enable device 100 to take up a larger footprint within the disc space once device 100 is expanded. Alternatively, device 100 can be inserted between adjacent vertebrae vertically (i.e., rotated about 90° from being on its side, as shown in FIG. 1E) such that when it is expanded in the disc space it expands vertically/longitudinally within the disc space to enable device 100 to expand the disc space once device 100 is expanded. Device is therefore able to occupy more lateral to medial and anterior to posterior space within the disc space relative to the size of the access.

In one embodiment, in its insertion and un-expanded state, device 100 is approximately 8 mm in height, approximately 11 mm in width (e.g., one end may have a larger width than the other) and approximately 31 mm in length. Device 100 can have many heights from 8 mm up to 16 mm. In embodiments, the width can go from 8-29 mm and the length from 22 mm-42 mm. When device 100 is expanded, the height remains the same, but the width can double or nearly double (from 11.5 to 22 mm or 47%) and the length can go from 26 mm to 20 mm (16% decrease). Device 100 can have many lordotic angles from 0 to 15 degrees or higher; the most common being 0, 4, 6, or 12 degrees. The top and bottom of device 100 can have different shapes to better fit the endplates such as football shaped or domed. Also, the different segments of device 100, separated by flexures 108, can be tailored or cut by wire EDM to create different horizontal expanded states such as oval, elliptical, circular, bean shaped, banana shaped or many other polygons and non-polygon shapes. The mean disc height at the L3-4 level is 11.3 mm+/−1.8 mm, L4-5 11.3+/−2.1 mm and L5-S1 10.7+/−2.1 mm. The average circumference of the L4 endplate of a patent is about 141 mm and surface area 1,492 $mm^2$ above. Device 100 can have different footprints to try to fill the endplate or disc space circumference. In embodiments, wire EDM can provide a greater improvement to the flexibility and tolerance of device 100, particularly for flexures 108 in the open or expanded configuration. In embodiments, in addition to wire EDM, improved flexibility and tolerance can be achieved by manufacturing device 100 out of biocompatible materials, for example, a shape memory material, which is described in greater detail below.

Referring now to FIGS. 1A-1F, device 100 can include a device body 102. Generally, device body 102 can be unitarily formed as a single monolithic construct, although multiple component embodiments are also contemplated. Device body 102 can include upper 104*a* and lower 104*b* bearing surfaces. As noted above, device 100 can be inserted generally on its side such that bearing surfaces 104*a*, 104*b* interface with and bear the forces of the adjacent vertebrae. Device body 102 can include a plurality of side body segments 106 unitary connected to each other by flexures 108. In embodiments, the flexures 108 can comprise a thin, flexible strip of material, including the material in which the entire device is constructed. Device body 102 can further include a first end body segment 112 and a second end body segment 114 that can also be connected with mediolateral body segments by flexures 108. Side body segments 106, end body segments 112, 114 and flexures 108 can perform a continuous, unitary outer perimeter surface. In some embodiments, device body 102 is configured to be inserted with first end body segment 112 distal of the surgeon, such that first end body segment 112 is an anterior body segment, second end body segment 114 is a posterior body segment, and side body segments 106 are mediolateral body segments. An interior 116 is defined between the body segments 106.

In the depicted embodiment, device 100 can include three mediolateral body segments 106 on each side such that device 100 includes a total of eight body segments 106. In some embodiments, a device having eight body segments may be generally octagonally shaped in the expanded configuration as depicted in FIGS. 2A-2E. In embodiments, segments 106 can include adjacent projections and grooves that form tongue and groove connections between adjacent segments 106 when the body is in the expanded configuration, wherein the tongue and groove connections can provide increased resistance of the body to shear and torsional forces. In other embodiments, device 100 may have greater or fewer mediolateral body segments on each side.

Device body 102 can further include a first internal locking bushing 118*a* with a corresponding second internal locking bushing 118*b* at the proximal end positioned at second end body segment 112. In embodiments, each locking bushing 118A and 118B can extend axially through the open interior 116 of device body 102. Locking bushings 118*a* and 118B can have a locking element which, in the depicted embodiment, takes the form of a pair of locking projections 119 and 121, respectively, on opposing sides of the distal end of locking bushing 118*a* and proximal end of locking bushing 118*b*, wherein each corresponding locking projection 119 and 121 protrudes from the locking bushings and within the open interior 116. When device 100 is expanded, locking bushings 118*a* and 118B are drawn together such that the locking projections 119 and 121 meet and are received together, configured to form corresponding locking or restricting mechanism which, in part, prevents further expansion of device 100. In embodiments, additional or alternative locking projections 119 and 121 can be incorporated and interlock with a corresponding locking element, wherein alternative sizes, positions, and other mechanisms that can be sufficient to, in part, restrict the expansion of the structure providing alternative footprint sizes to fill the endplate or disc space circumference when implanted. Once device 100 is expanded, these locking elements can prevent further expansion once the projections 119 and 121 are coupled together, which prevents damage to device body 102 that may otherwise result from over-expansion.

Locking bushings 118*a* and 118*b* can include an open interior 124 that can accommodate bone growth material and one or more openings along one or more sides of the locking bushings in communication with the open interior. In some embodiments, multiple devices can be provided with locking bushings 118*a* and 118*b* of different lengths. Devices having locking bushings 118*a* and 118*b* of various axial lengths provide a surgeon with the flexibility to select a device with a desired degree of expansion for the needs of a given patient. For example, the disc space may not be large enough to accommodate a fully expanded device, so a device having a longer locking bushing can be selected to limit expansion to a predetermined amount that best fits the disc space. In other embodiments, locking bushings 118*a* and 118*b* are not unitarily formed with device body such that a surgeon can select a locking bushing from a plurality of different locking bushings having different axial lengths, which is then functionally linked to device body with an expansion screw (described in more detail below). In embodiments, the locking bushings can be attached to the body 100 with an expansion tool, allowing for quick and efficient interchangeability.

Figure 4B:
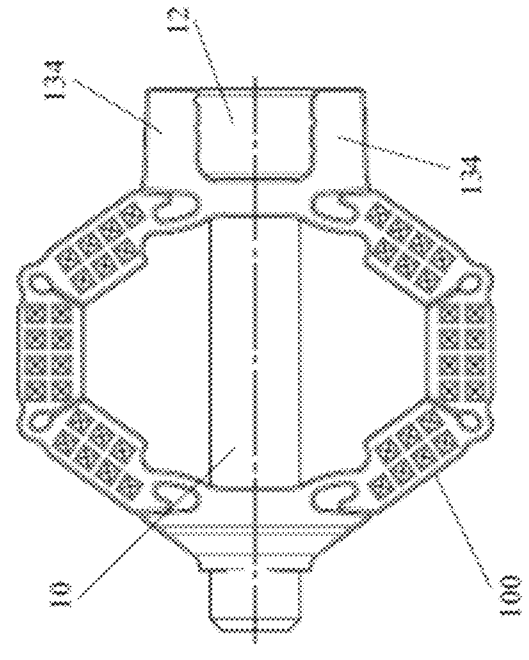
FIGS. 4A-4B depict an expandable intervertebral body fusion device according to an embodiment.
Figure 4A:
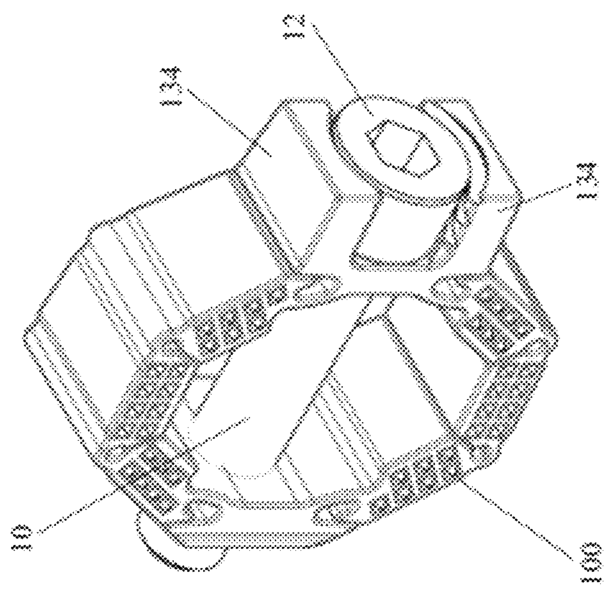

Each of first end body segment 112 and second end body segment 114 can include an opening that assists in insertion and/or expansion of device. In one embodiment, second end body segment 114 includes a second opening 130 and first end body segment 112 includes a first opening 132. A stabilizing element, such as a screw 10 (See FIGS. 4A-4B) can extend through second opening 130 and locking bushings 118*a* and 118*b* and into the first opening 132, which, in the case of the stabilizing element being a screw, may be threaded to interface with the threads of the screw. Second end body segment 114 can further include a pair of flanges 134 that define an opening 130 in which a screw head 12 of a stabilizing screw 10 can be contained. Flanges 134 can also define outer gripping surfaces that can be engaged by an insertion element used to insert device 100 into the patient's body. In some embodiments, first end body segment 112 can be tapered to facilitate insertion of device 100 into the disc space through the minimally invasive access opening.

FIGS. 2A-2E depict device 100 in an expanded configuration. As device 100 is expanded, the mediolateral body segments 106 on opposing sides of device body 102 are moved away from each other causing the device to expand medially and laterally within disc space 116 and, therefore, providing a larger area to facilitate bone growth within device 100. Device 100 can be expanded until the locking bushing 118*a* and 118*b* reach, approximately, the center of device 100 within the interior 116 such that the locking projections 119 and 121 of the locking bushing 118*a* and 118*b* are coupled together, which form a locking mechanism to prevent further expansion. As can be seen in these figures, expanded device 100 provides a continuous outer perimeter having a greater width (i.e., mediolateral width when device 100 is horizontally expanded) between side body segments 106 and a corresponding larger interior 116 into which bone growth promoting material can be inserted through first opening 130 and openings in locking bushing 118*a* and 118*b*. In some embodiments, the locking projections 119 and 121 of the locking bushing 1118*a* and 118*b* can permanently lock into place via locking phalanges stabilizing the implant without the need of a stabilizing screw. In other embodiments, a stabilizing screw 10 can be inserted through device and extend through second opening 130 and be threadedly engaged with first opening 132 to provide further support and stability for device in vivo (See FIGS. 4A-4B). In some embodiments, a head of such a screw may be contained between flanges 134. In other embodiments, device 100 can remain in the body with no screw or other supporting member extending through device.

Figure 3A:
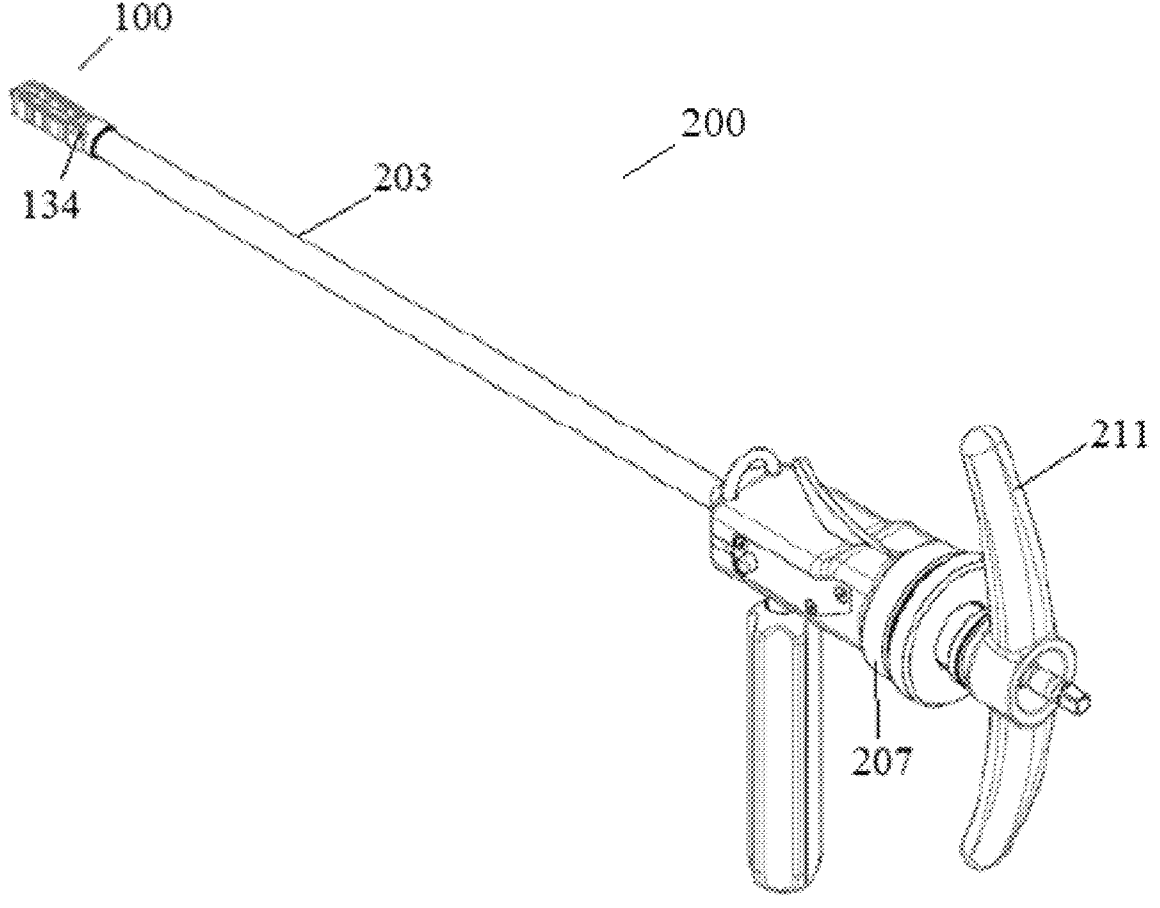
FIGS. 3A-3C depict a device for inserting and expanding and expandable intervertebral body fusion device according to an embodiment.
Figure 3B:
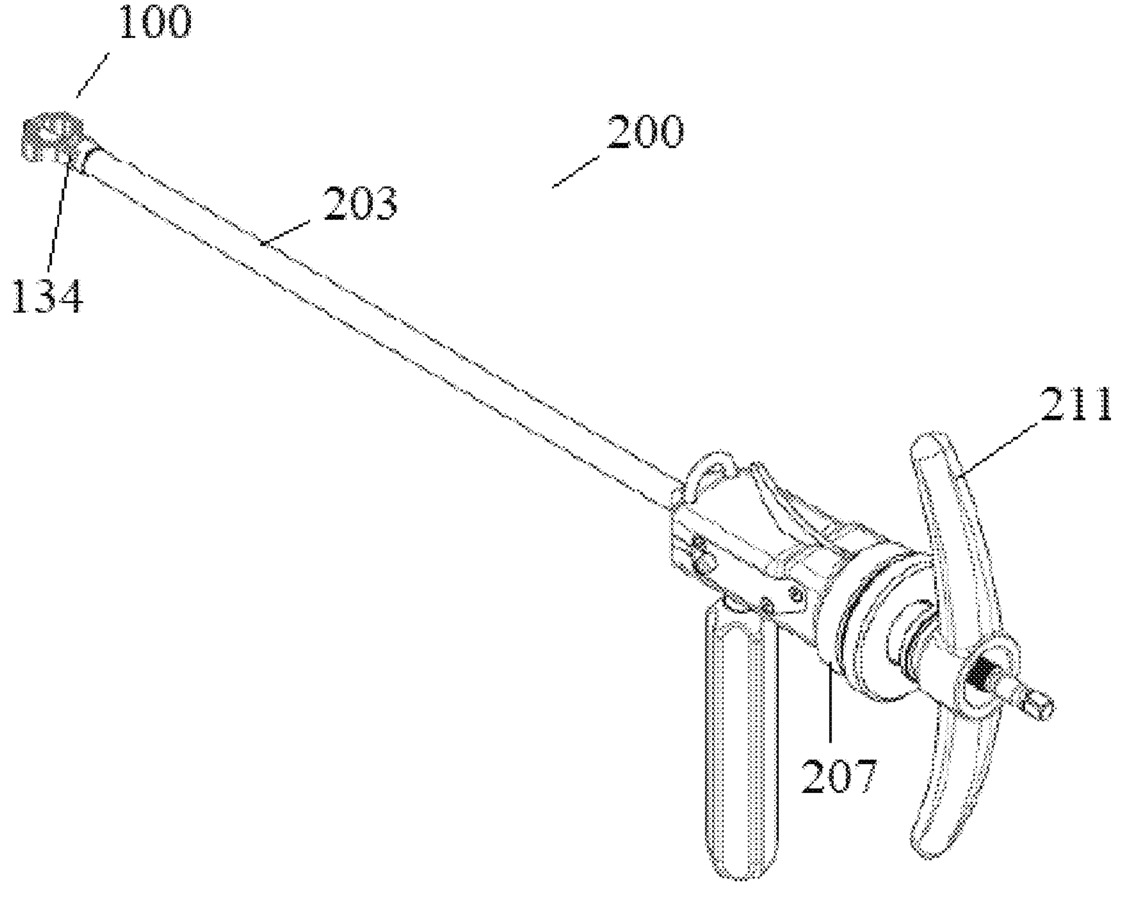
Figure 3C:
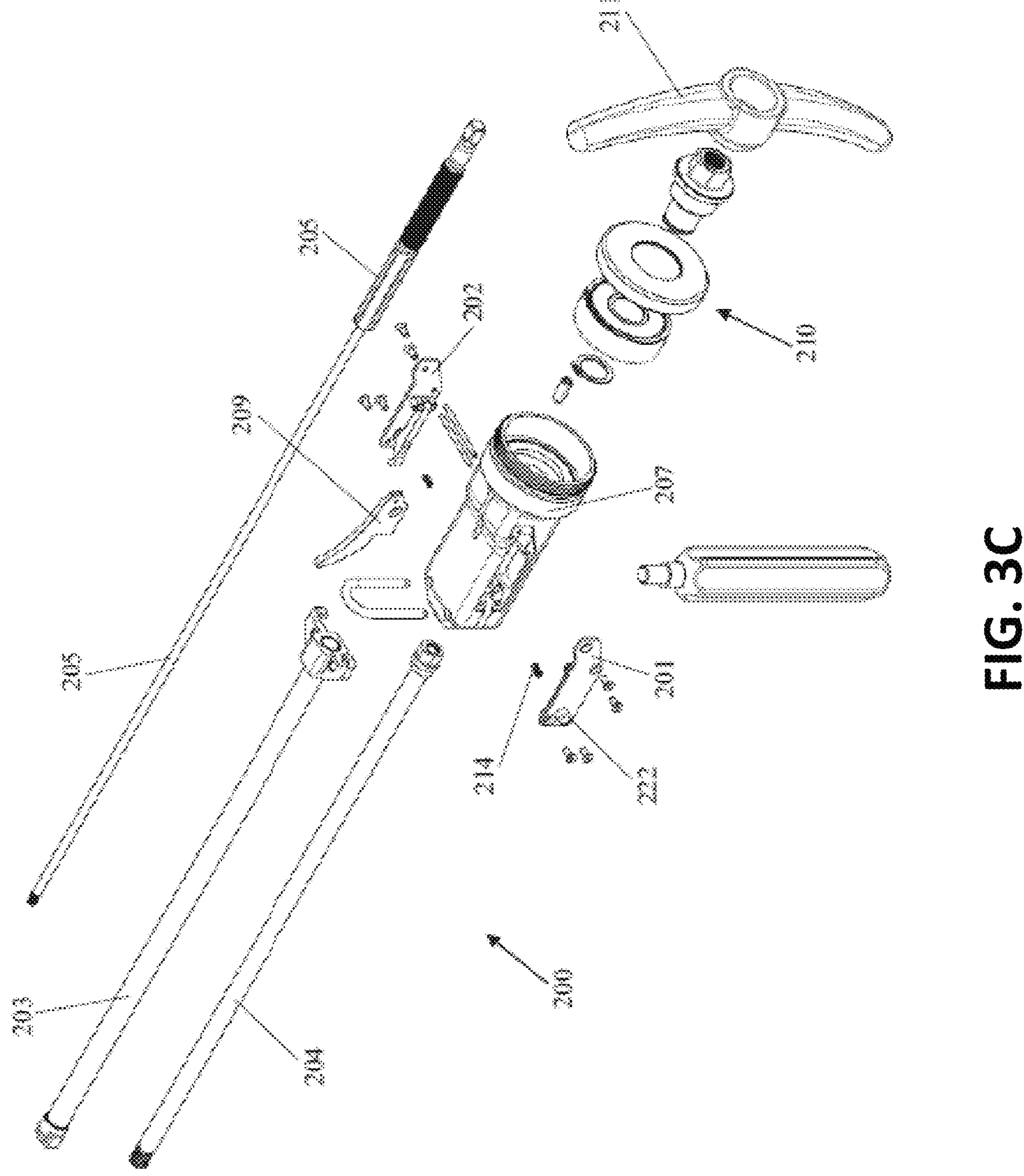

FIGS. 3A-3C depict an embodiment of an insertion device 200 that can be used to implant and extract an expandable intervertebral body fusion device as disclosed herein. In embodiments, the insertion device 200 can be used to assist in the expansion of the body 102. In embodiments, the insertion device 200 can also assist in undoing the expanded implant to its original insertion shape for removal. Insertion device 200 can include an attachment rod 203 configured to grip the outer surfaces of flanges 134 of device 100, a stabilizing rod 204 having a threaded distal end configured to attach to the threaded inner surfaces of flanges 134 and to be extended through attachment rod 203 and an expansion rod 205 configured to be extended through stabilizing rod 204 and having a threaded distal end configured to interface with first opening 130 in device 100 to expand device 100. In operation, expansion rod 205 can be actuated, at least in part, by rotating handle 211 that interfaces with expansion rod 205 and housing 207 via handle assembly 210. To prevent rotation of expansion rod 205, key lock 209 can be actuated to insert key lock 209 into a slot 220 in expansion rod 205. Rotation of handle 211 can, therefore, help cause the expansion element 205 to pull the distal end of the implant back towards the proximal end, which can expand the implant. The expanded implant can also be, at least in part, reversed into its insertions state (straightened) by rotating handle 211 counterclockwise. This would assist in the removal of an expanded implant after insertion into the disc space. Following expansion, one or more buttons 222 can be actuated to disengage sprint 214 loaded latches 201, 202 from housing 207, to enable housing 207 to be detached. Expansion rod 205 can also be detached by releasing the key lock and rotating the rod to disengage from the threaded distal opening of the implant. Next, the stabilizing rod 204 can be detached. One or more of bone graft and a stabilizing screw 10 (as described above) can be inserted through attachment rod 203 before the attachment rod 203 is detached to complete the insertion and expansion procedure.

As noted above, device 100 can be inserted between adjacent vertebrae on its side, with bearing surfaces 104*a*, 104*b* configured to interface with the vertebrae. Device 100 can be inserted in a collapsed configuration and then expanded within the disc space to occupy a greater footprint within the disc space. In embodiments, device 100 can be inserted through the back muscles similar to the approach used for a posterior lumbar interbody fusion (PLIF) procedure. Expansion of device 100 then provides a large area within the device to promote bone growth similar to the size of anterior lumber interbody fusion (ALIF) procedure. Use of device 100 in this manner therefore enables the greater fusion capabilities of an ALIF procedure without the greater trauma and risk associated with accessing the disc space through the abdominal muscles. Other access approaches and device orientations are possible including lateral abdominal retroperitoneal insertion and anterior retroperitoneal insertion with larger sizes. Also, anterior and posterior cervical insertions with smaller sizes. One example of a type of insertion device that may be adapted for use with the cage device 100 disclosed herein is disclosed in U.S. Patent Publication No. 2020/0281743, previously incorporated by reference herein.

In embodiments, device 100 can be manufactured by wire electrical discharge machining (wire EDM), 3D printed, or other alternative manufacturing methods that can produce device as disclosed herein. In order to construct device 100 using wire EDM, the locking bushings 118A and 118B can be constructed in two pieces rather than constructed as a single piece, in comparison to commonly owned U.S. application Ser. No. 17/866,896, which is incorporated by reference herein in its entirety. In embodiments, the two-piece construction of bushings 118A and 118B is implemented in order to enable manufacturing via wire EDM, in contrast to the device in application Ser. No. 17/866,896.

Device 100 can be formed from various biocompatible materials, for example, a shape memory material such as Nitinol (NiTi), also known as Nickel/Titanium. In embodiments, the composition of Nickel included in the NiTi can be 54-57 weight percent. In embodiments, the composition of Nickel and Titanium included in the NiTi can be 50:50 weight percent. In embodiments, F2063 NiTi may be used to construct device 100. An example composition of F2063 NiTi is provided in TABLE 1 below. It will be understood that wire EDM can include the same or similar composition of NiTi, thus meeting American Society for Testing and Materials (ASTM) F2063 designation.

TABLE 1

Chemical Composition Requirements

| Element | % (mass/mass) |
|---|---|
| Nickel | 54.5 to 57.0 |
| Carbon, maximum | 0.040 |
| Cobalt, maximum | 0.050 |
| Copper, maximum | 0.010 |
| Chromium, maximum | 0.010 |
| Hydrogen, maximum | 0.005 |
| Iron, maximum | 0.050 |
| Niobium, maximum | 0.025 |
| Nitrogen, maximum | 0.005 |
| Oxygen, maximum | 0.040 |
| Titanium[A] | Balance |

[A]Approximately equal to the difference between 100% and the sum percentage of the other specified elements. The percentage titanium content by difference is not required to be reported.

Constructing device 100 out of NiTi provides an elastic material capable of expanding and retracting without breaking, while maintaining and improving durability, flexibility, and tolerance. Meaning, device 100 can be implanted (i.e., expanded), to act as a stabilizer for force distribution between vertebral bodies and to restore or, at least, partially restore the height of the intervertebral and foramina space. Device 100 can also be removed and re-inserted (i.e., retracted and re-expanded) from the intervertebral portion of an intervertebral body fusion as many times as necessary without breaking or deteriorating over time. Other, inferior devices made from other less sturdy and less manipulatable materials, in contrast, can be prone to breaking when repeatedly expanded and contracted. In embodiments, a device 100 comprising a shape memory material can be configured to be cooled, heated, or annealed to a specific or range of temperatures to maintain or adapt to conform to a particular shape (e.g., depending on the temperature of device 100, device 100 can maintain a particular shape). For example, device 100, at a heated temperature, can be set to and maintain the expanded position.

In embodiments, upon cooling or introducing a cooling solution to a device that is at the heated temperature, device 100 can be automatically transitioned into the unexpanded position (i.e., straightened) in an insertion state when device 100 falls below the threshold "heated" temperature. A cooling solution can therefore be used to reverse the effect of expanding into or maintaining the octagonal shape when device 100 is heated. In embodiments, the cooling solution can, at least in part, make device 100 smaller, which can assist in the removal of the implant from the body (which has a higher temperature than the ambient temperature of an operating room). Thus, use of the cooling solution on device 100 can cause device 100 to retract, at least in part, into the nonexpanded position, which makes removal of the implanted device easier. In some embodiments, insertion device 200 can assist in retracting device 100 out of the octagonal shape for removal and remove device 100 from the patient. Such a cooling effect or implementing a cooling solution may be done at a later time in a separate procedure following initial implantation device 100. For example, cooling and removal of device 100 can be implemented to retrieve the implant for maintenance or replacement.

In embodiments, the heated temperature at which device 100 will automatically expand can be in the range of 33-37° C. (i.e., at or near body temperature). As such, the cool temperature for device 100 to remain in the unexpanded position can be below approximately 33° C. such that device 100 will remain in the unexpanded position in typical room temperature conditions. In embodiments, the implant can be stored at room temperature in the pre-insertion state (e.g., approximately 20-22° C.) and will therefore remain in the current state in which it is stored (e.g., the unexpanded/straightened state). In some embodiments, a reduction or elimination of the need of an insertion device 200 to expand and retract device 100 can be realized due to the automatic temperature-based expansion and contraction of device 100. However, in some embodiments, an insertion device 200 can still be used to aid in expanding and contracting device 100.

In embodiments, when device 100 is implanted, initially in the collapsed state (e.g., as device 100 is at room temperature and not yet heated to initiate transition from the collapsed state to the expanded state), it may be positioned in the body and be heated (e.g., heated from the internal temperature of the body). Once implanted, when a threshold temperature is reached due to the exposure to the natural increase in body temperature, approximately 33-37° C., the implant can, in part or completely, expand or initiate expansion into the octagonal shape (i.e., open into the expanded position). The implant will expand into the octagonal shape as the temperature of the implant increases naturally due to the natural increase in temperature from the body in which the implant is implanted (i.e., body temperature being greater than room temperature in which it can be stored). As noted above, in some embodiments, insertion device 200 can assist in expanding device 100 into the octagonal shape after insertion into the body. It is to be understood that, in embodiments, device 100 can be configured to be set in a configuration and adjustable between expanded configurations, retracted configurations, or otherwise configuration in-between, at alternative temperatures.

Figure 5:
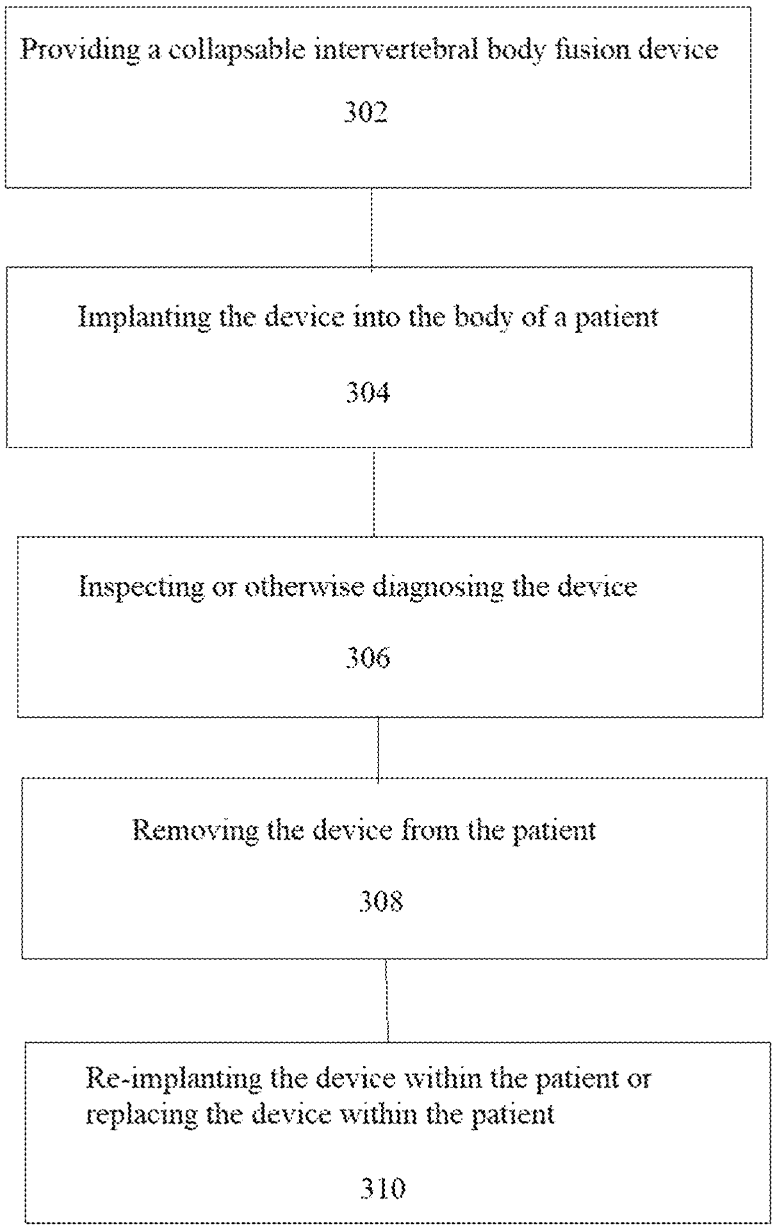
FIG. 5 depicts a flowchart illustrating the implementation of an expandable intervertebral body fusion device, according to embodiments.

FIG. 5 depicts a flowchart illustrating the implementation of an expandable intervertebral body fusion device described herein, according to embodiments. At 302 an expandable intervertebral body fusion device can be provided in a collapsed configuration. In embodiments, the expandable intervertebral body fusion device can be maintained in the collapsed configuration until a threshold temperature of the shape memory material, from which the device is made, is achieved. In embodiments, the threshold temperature is above typical room temperature and the expandable intervertebral body fusion device can alter or otherwise transition into an alternative configuration when the temperature of the expandable intervertebral body fusion device exceeds a threshold temperature, which may be at or near body temperature. At 304, the expandable intervertebral body fusion device can be implanted into the body of a patient, in the collapsed configuration. In embodiments, device 100 can expand into an expanded configuration, due to an increase in temperature from the body in which device 100 is implanted. The expansion can provide an increase in the footprint size that can fill the endplate or disc space circumference when implanted within a patient. An insertion device may or may not be used to aid in the natural temperature-based expansion of device 100. At 306, device 100 may experience wear/tear or shift within the patient, required check-ups, or otherwise suggest or be inclined to be inspected at a later time after initial implantation at step 304. At 308, device 100 can be removed from the body by subjecting device 100 to cooling, wherein device 100 is cooled below the threshold temperature. In embodiments, the cooling of device 100 can transition device 100 from an expanded configuration to a retracted configuration. In embodiments, a cooling solution can be exposed to device 100 to cool the shape memory material and to transition device 100 from the expanded configuration to the retracted configuration. Once in the retraced configuration, device 100 can be more easily removed from the patient with a smaller, more discrete, or slim insertion/extraction area of the patient. At 310, device 100 can be reinserted into the body of the patient or an alternative device implanted, wherein device 100 can be expanded or re-expanded within the patient based on the experienced increase in temperature (e.g., the body temperature of the patient being greater than room temperature, in which device 100 can be stored).

In some embodiments, devices described herein can be manufactured in a partially open/closed configuration, rather than being either fully opened or fully closed (such as, for example, 25% open, 50% open, 75% open, etc.), which can increase longevity of the device through multiple opening and closing cycles. In some such embodiments in which the device comprises a shape memory material, the device can be manufactured partially opened/closed and heat set to fully open such that when the device cools it will automatically return to the partially open/closed configuration and can be fully closed with an insertion device as described herein.

U.S. Patent Publications No. 2020/0281739 and 2020/0281743 and U.S. patent application Ser. No. 17/866,896 are hereby incorporated by reference herein in their entireties.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112 (f) are not to be invoked unless the specific terms “means for” or “step for” are recited in a claim.

The invention claimed is:

1. An expandable intervertebral body fusion device, comprising:

a unitary monolithic body having a plurality of body segments coupled to each other with flexure members and an opening defined between the plurality of body segments;

a first locking bushing extending from a first end body segment into the opening;

a second locking bushing extending from a second end body segment into the opening; and wherein the body is configured to be mediolaterally expanded from a compressed configuration to an expanded configuration causing the plurality of body segments to generally move away from each other to expand the opening between the plurality of body segments such that the body forms a greater mediolateral footprint in the expanded configuration than in the compressed configuration, and wherein the first and second locking bushings are brought together within the opening and further expansion of the body is prevented by the interaction between the first and second locking bushings, wherein the first locking bushing or the second locking bushing are attached to the body with an expansion tool, the device further comprising a plurality of locking bushings having different axial lengths, wherein each different axial length is configured to permit a predetermined amount of expansion of the body.

2. The expandable intervertebral body fusion device of claim 1, wherein the intervertebral body fusion device is constructed by wire EDM.

3. An expandable intervertebral body fusion device, comprising:

a unitary monolithic body having a plurality of body segments coupled to each other with flexure members and an opening defined between the plurality of body segments, including:

a first end body segment having a portion extending into the opening; and a second end body segment having a portion extending into the opening; and wherein the body is configured to be mediolaterally expanded from a compressed configuration to an expanded configuration to expand the opening between the plurality of body segments such that the body forms a greater mediolateral footprint in the expanded configuration than in the compressed configuration, and wherein the portion of the first end body segment extending into the opening and the portion of the second end body segment extending into the opening are brought together within the opening to prevent further expansion of the body.

4. The expandable intervertebral body fusion device of claim 3, wherein the portion of the first end body segment extending into the opening and the portion of the second end body segment extending into the opening interlock together.

5. The expandable intervertebral body fusion device of claim 3, wherein the first end body segment and second end body segment each define an opening configured to receive an expansion tool therethrough.

6. The expandable intervertebral body fusion device of claim 3, where the first end body segment and the second end body segment each define an open interior configured to receive bone growth material therein.

7. The expandable intervertebral body fusion device of claim 3, wherein the plurality of body segments form tongue and groove connections with each other in the expanded configuration.

8. The expandable intervertebral body fusion device of claim 7, wherein the tongue and groove connections provide the body with increased resistance to shear and torsional forces.

9. The expandable intervertebral body fusion device of claim 3, wherein the portion of the first end body segment extending into the opening and the portion of the second end body segment extending into the opening prevent damage to the body from overexpansion.

* * * * *